United States Patent [19]
Clawson et al.

[11] Patent Number: 6,095,135
[45] Date of Patent: Aug. 1, 2000

[54] APPARATUS FOR PROVIDING BENEFITS TO RESPIRATORY GASES

[75] Inventors: Burrell E. Clawson, Newport Beach, Calif.; James Weigl, Las Vegas, Nev.

[73] Assignee: Enternet Medical, Inc., Las Vegas, Nev.

[21] Appl. No.: 09/113,649

[22] Filed: Jul. 10, 1998

[51] Int. Cl.[7] .................................................. A61M 16/00
[52] U.S. Cl. ................................ 128/201.13; 128/203.12; 128/205.27; 128/205.28
[58] Field of Search ..................... 128/201.13, 203.12, 128/205.25, 205.27, 205.26, 205.24, 205.28, 205.29, 205.12

[56] References Cited

U.S. PATENT DOCUMENTS

| | | |
|---|---|---|
| 3,612,048 | 10/1971 | Takaoka et al. ................... 128/205.28 |
| 3,615,233 | 10/1971 | Doebieg et al. ................... 128/205.28 |
| 3,721,238 | 3/1973 | Wise et al. . |
| 3,747,598 | 7/1973 | Cowans . |
| 3,782,081 | 1/1974 | Munters . |
| 3,932,153 | 1/1976 | Byrns . |
| 4,036,616 | 7/1977 | Byrns . |
| 4,040,804 | 8/1977 | Harrison . |
| 4,054,134 | 10/1977 | Kristzer ............................ 128/205.24 |
| 4,063,913 | 12/1977 | Kippel et al. . |
| 4,090,513 | 5/1978 | Togawa . |
| 4,108,172 | 8/1978 | Moore, Jr. . |
| 4,133,656 | 1/1979 | Kippel et al. . |
| 4,148,732 | 4/1979 | Burrow et al. . |
| 4,168,706 | 9/1979 | Lovell . |
| 4,171,962 | 10/1979 | Kippel et al. . |
| 4,172,709 | 10/1979 | Kippel et al. . |
| 4,181,511 | 1/1980 | Kippel et al. . |
| 4,181,512 | 1/1980 | Kippel et al. . |
| 4,192,301 | 3/1980 | Hardwick ........................ 128/205.24 |
| 4,200,094 | 4/1980 | Gedeon et al. . |
| 4,224,939 | 9/1980 | Lang . |
| 4,297,117 | 10/1981 | Holter et al. . |
| 4,325,364 | 4/1982 | Evans ............................... 128/201.13 |
| 4,360,018 | 11/1982 | Choksi . |

(List continued on next page.)

*Primary Examiner*—John G. Weiss
*Assistant Examiner*—V. Srivastava
*Attorney, Agent, or Firm*—Stout, Uxa, Buyan & Mullins; Frank J. Uxa

[57] ABSTRACT

Apparatus for heating and humidifying respiratory gases include a housing, a gas permeable member positioned in the housing to exchange heat and moisture with respiratory gases passing through the housing, a fitting joined to both the housing and a tracheal tube device, and a fitting closure assembly movable to open and close a second end opening of the fitting. In one embodiment, the apparatus includes a bypass line positioned to pass inspiratory gases to the fitting and tracheal tube device without passing through the housing. This bypass line embodiment is very effective in providing an additional treatment, for example, a nebulizer treatment, to the patient. The present apparatus are particularly structured and adapted to reduce the risk of causing trauma to the patient and to reduce clinician anxiety.

20 Claims, 4 Drawing Sheets

U.S. PATENT DOCUMENTS

| | | | |
|---|---|---|---|
| 4,367,734 | 1/1983 | Benthin . | |
| 4,382,440 | 5/1983 | Kapp et al. | 128/205.28 |
| 4,458,679 | 7/1984 | Ward . | |
| 4,516,573 | 5/1985 | Gedeon . | |
| 4,566,480 | 1/1986 | Parham | 128/205.24 |
| 4,597,917 | 7/1986 | Lunsford . | |
| 4,707,167 | 11/1987 | Saito et al. . | |
| 4,771,770 | 9/1988 | Artemenko et al. . | |
| 4,790,832 | 12/1988 | Lopez | 128/912 |
| 4,829,997 | 5/1989 | Douwens et al. . | |
| 5,016,628 | 5/1991 | Lambert . | |
| 5,022,394 | 6/1991 | Chmielinski . | |
| 5,035,236 | 7/1991 | Kanegaonkar . | |
| 5,038,767 | 8/1991 | Jumpertz . | |
| 5,109,471 | 4/1992 | Lang . | |
| 5,143,060 | 9/1992 | Smith | 128/205.28 |
| 5,172,686 | 12/1992 | Anthony . | |
| 5,195,527 | 3/1993 | Hicks . | |
| 5,213,096 | 5/1993 | Kihlberg et al. . | |
| 5,228,435 | 7/1993 | Smith . | |
| 5,230,727 | 7/1993 | Pound et al. . | |
| 5,255,674 | 10/1993 | Oftedal et al. . | |
| 5,320,096 | 6/1994 | Hans . | |
| 5,333,607 | 8/1994 | Lee et al. | 128/292.27 |
| 5,337,739 | 8/1994 | Lehman . | |
| 5,349,946 | 9/1994 | McComb | 128/203.12 |
| 5,360,002 | 11/1994 | Smith . | |
| 5,383,447 | 1/1995 | Lang . | |
| 5,386,825 | 2/1995 | Bates . | |
| 5,390,668 | 2/1995 | Lehman . | |
| 5,435,298 | 7/1995 | Anthony . | |
| 5,435,299 | 7/1995 | Langman . | |
| 5,460,172 | 10/1995 | Eckerbom et al. | 128/201.13 |
| 5,462,048 | 10/1995 | Lambert et al. . | |
| 5,468,451 | 11/1995 | Gedeon . | |
| 5,482,031 | 1/1996 | Lambert . | |
| 5,487,382 | 1/1996 | Bezicot . | |
| 5,505,768 | 4/1996 | Altadonna . | |
| 5,546,930 | 8/1996 | Wikefeldt . | |
| 5,558,088 | 9/1996 | Smith . | |
| 5,570,684 | 11/1996 | Behr . | |
| 5,577,494 | 11/1996 | Kuypers et al. . | |
| 5,590,644 | 1/1997 | Rosenkotter . | |
| 5,640,952 | 6/1997 | Swann et al. | 128/205.27 |
| 5,647,344 | 7/1997 | Turnbull . | |
| 5,660,173 | 8/1997 | Newton | 128/205.28 |
| 5,931,163 | 8/1999 | Stegmann et al. | 128/204.28 |

APPARATUS FOR PROVIDING BENEFITS TO RESPIRATORY GASES

BACKGROUND OF THE INVENTION

The present invention relates to apparatus useful to provide benefits to respiratory gases. More particularly, the invention relates to apparatus for heating and humidifying respiratory gases, and preferably in providing additional treatments to patients.

During surgery and other medical procedures, a patient is frequently connected to an anesthesia machine or ventilator to provide respiratory gases to the patient. The respiratory gases passed to the patient are advantageously heated and humidified so that the gases entering the patient are of a suitable temperature and humidity so as not to adversely impact the patient. Heat and moisture exchangers (HMEs) are often used to provide heat and humidity to the respiratory gases entering the patient. Typically, these HMEs are located so that respiratory gases from the patient pass through a tracheal tube into the HME, often a fibrous or other gas permeable material, which accumulates or collects heat and moisture from the exhaled gases. During the inhaling of respiratory gases, for example, from an anesthesia machine, the HME provides both heat and moisture to these respiratory gases prior to the gases entering the patient. Over a period of time, the HME is effective to maintain a certain level of temperature and humidity in the respiratory gases entering the patient.

Such HMEs do, however, have certain drawbacks. Thus, HME unites currently commercially available have configurations and structures which can cause clinician anxiety and patient trauma, for example, when the patient using the HME is to receive an additional treatment, for example, a nebulizer treatment or like treatments.

To illustrate, using currently commercially available HME units and patient manifolds, when an additional treatment is to be provided to the patient, the HME unit and/or patient manifold is disconnected from the patient and the device for providing the additional treatment is connected to the patient to provide the additional treatment. During the interim, that is between the disconnection of the HME unit/patent manifold and the connection of the additional treatment device, the patient is depressurized and without external mechanical breathing support. Any failure to quickly connect the additional treatment device can result in substantial trauma to the patient, particularly when the patient is a child or infant or otherwise in critical cardiopulmonary condition. Also, the need for the clinician to rapidly and effectively connect the additional treatment device does create a high level of clinician anxiety which can result in clinician ineffectiveness, ultimately resulting in increased risk of harm to the patient. Experience has shown, even with quick reconnection, conscious patients experience anxiety induced higher pulse rates and blood pressure.

Wikefeldt U.S. Pat. No. 5,546,930 discloses a device including a bypass line which bypasses respiratory gases from a ventilator or anesthesia machine through a nebulizer into the tracheal tube of the patient. However, this patent discloses that the bypass line withdraws respiratory gases downstream of the in line filter which can result in less effective bypass of the respiratory gases. Also, the patent still requires that plugs be physically removed to allow flow in the bypass line. Such plug removal from the bypass line results in a depressurization of the unit and a resulting increase in clinician anxiety/patient trauma, as discussed above.

It would be advantageous to provide apparatus by which respiratory gases can be effectively and reliably heated and humidified and which can be effectively used in providing additional treatments to the patient so that the comfort and safety of the patient is enhanced and the stress on the clinician is reduced.

SUMMARY OF THE INVENTION

New apparatus for heating and humidifying respiratory gases, and preferably for use in providing additional treatments to the patients, have been discovered. Such apparatus provide for exchanging heat and moisture with respiratory gases exhaled (expiratory gases) by the patient and providing heat and moisture to the respiratory gases being inhaled (inspiratory gases) by the patient. In general, the present apparatus are more patient and clinician friendly, that is provide for increased comfort and/or safety and/or reduced trauma to the patient undergoing surgery or other treatments and/or reduced clinician anxiety, than the current commercially available HMEs and patient manifolds. Various features of the present invention provide enhancements as to the comfort and safety of the patient and reduced clinician stress so that the use of the present apparatus effectively provides heat and moisture, and preferably additional treatments to respiratory gases with reduced, if any, adverse effects on the patient and the clinician. These benefits are obtained with apparatus which are straightforward in construction, easy and relatively inexpensive to manufacture and use, and are effectively controlled to provide the results desired.

Generally, the present invention is directed to apparatus for treating or modifying respiratory gases.

Such apparatus typically comprise a housing, and a gas permeable member, and preferably a filter element. The housing has an inlet adapted for connection to a tracheal tube device and an outlet adapted for connection to a tube or tubes for passing respiratory gases, for example, to and from an anesthesia machine, ventilator and the like. The inlet and the outlet are positioned so that respiratory gases passing through the housing pass therebetween. The gas permeable member is positioned in the housing between the inlet and the outlet and is adapted to exchange heat and moisture with respiratory gases passing through the housing. The filter element is located in the housing and is adapted to filter respiratory gases passing through the housing. Preferably, the housing is designed to be compact and to reduce the amount of dead space between the tracheal tube device and the tube (or tubes) for passing respiratory gases. The compact housing allows the apparatus to be used and perform its functions more unobtrusively, relative to prior art HME devices. The reduced dead space increase the use efficiency of heat and moisture passing into and/or generated in the housing.

One aspect of the present invention is directed to apparatus which comprise a housing having an inlet and an outlet, as described herein, a gas permeable member, as described herein, a fitting and a fitting closure assembly. The fitting is joined to both the housing and the tracheal tube device, and includes a separate opening through which an additional treatment, for example, to the lungs of the patient, is provided to the patient, for example, while by passing the filter/HME. The fitting closure assembly is coupled to the fitting and includes a through port adapted to be coupled to a device for providing the additional treatment. The fitting closure assembly is moveable between a first position in which the separate opening is not in fluid communication with the through port and a second position in which the separately opening is in fluid communication with the through port.

The fitting closure assembly preferably is rotatable relative to the fitting. This rotation of the fitting closure assembly moves this assembly between the first and second positions. The apparatus preferably further comprises a cap assembly, more preferably, secured to the fitting, adapted to cover the through port when the through port is not coupled to a device for providing an additional treatment. The fitting closure assembly preferably further includes a spaced apart second through port, for example, through which respiratory gases, in the fitting, are monitored. Preferably, when the fitting closure assembly is in the first position, the separate opening is in fluid communication with the second through port.

In a very useful embodiment, the fitting closure assembly is rotatable relative to the fitting between spaced apart first and second rotation stops located on the fitting. Such spaced apart rotation stops very effectively limit the rotation of the fitting closure assembly and provide a positive indication of the position of the fixture closure assembly relative to the fitting.

The present apparatus preferably include a generating material located in the housing between the inlet and the outlet and adapted to generate water available to humidify respiratory gases passing through the housing. A hygroscopic component is preferably positioned in the housing separate and apart from the gas permeable membrane and the generating material. Hygroscopic material, such as calcium chloride and the like, is adapted to generate heat available to heat respiratory gases passing through the housing. The use of a separate hygroscopic component effectively provides a very quick heat input to the respiratory gases being passed to the patient without adversely interfering with the operation of the other components in the housing. Such a hygroscopic component very effectively reduces patient trauma and increases patient comfort, particularly during the start up of the present apparatus.

The above-noted apparatus are very useful when secondary treatments are required to be provided. The ability to move the fitting closure assembly between first and second positions is effective so that the additional or secondary treatment apparatus can be hooked up or connected to the fitting closure assembly and pressurized prior to opening the separate opening to the through port. No substantial or significant interruption in the patient's respiratory gas flow occurs as a result of providing the additional treatment. This reduces stress on the clinician providing the secondary treatment and/or reduces trauma on the patient receiving the secondary treatment and/or reduces the need for other equipment needed to maintain gas transfer to the patient during the secondary treatment.

In another broad aspect of the present invention, apparatus for heating and humidifying respiratory gases passed to a patient are provided and comprise a housing, a filter element, a gas permeable member, and a fitting, each as described elsewhere herein. In addition, these apparatus further comprise a bypass line including a first portion adapted to be connected to and in fluid communication with both the tube for passing inspiratory gases and a device for providing the additional treatment, and a second portion adapted to be connected to and in fluid communication with a device for providing the additional treatment and the fitting. Further, a valve is provided and is adapted to be moved between a closed position in which no gas flow occurs through the bypass line and an open position in which inspiratory gases from the tube for passing inspiratory gases to the fitting flows through the bypass line.

This valve is preferably positioned to move between the closed position in which the first portion of the bypass line is not in fluid communication with the tube for passing inspiratory gases and the open position in which the first portion of a bypass line is in fluid communication with the tube for passing inspiratory gases. Any suitable valve configuration effective to provide the described functions may be employed in accordance with the present invention. Such valve should be such that little or no depressurization of the housing or the tracheal tube device occurs as a result of the movement of the valve between the open and closed positions, for example, in the fraction of a second needed to switch positions. Preferably, the valve in the inspiratory line is switched during exhalation to reduce the need for speed in switching the valve.

In one very useful embodiment, the valve comprises a sleeve valve secured to the tube for passing inspiratory gases. Such apparatus preferably further comprise a fitting closure assembly coupled to the fitting and including a through port adapted to be coupled to and in fluid communication the second portion of the bypass line. This fitting closure assembly is moveable between a first position in which the separate opening of the fitting is not in fluid communication with the through port of the closure assembly and a second position in which the separate opening is in fluid communication with the through port. The fitting closure assembly described immediately above may be configured substantially similarly to the fitting closure assembly discussed previously.

In addition, such apparatus may further comprise a generating material located in the housing between the inlet and the outlet and adapted to generate water available to humidify respiratory gases passing through the housing. Also, a hygroscopic component, separate and apart from the other components within the housing can be employed, as described elsewhere herein.

Methods for heating and humidifying respiratory gases passed to a patient and for providing an additional treatment to the patient are included within the scope of the present invention. Such methods include operating the apparatus described herein so that the fitting is joined to a tracheal tube located within the patient, thereby providing respiratory gases to the patient. A device, such as a nebulizer or a like device, for providing one or more treatments, for example, to the patient, is provided. Inspiratory gases from the tube for passing inspiratory gases is caused to pass through the bypass line into the fitting. The device for providing the additional treatment to the patient is operated so as to provide the additional treatment to the patient through the second portion of the bypass line.

The present methods preferably further comprise preventing inspiratory gases passing through the bypass line, and causing the device for providing the additional treatment to the patient to be inoperative.

In a further embodiment, where the present apparatus includes a fitting closure assembly as described herein, the fitting closure assembly is moved from the first position to the second position after the causing step is initiated. This embodiment provides for additional safety in that the fitting and tracheal tube are not depressurized as a result of the additional treatment being provided to the patient.

Commonly assigned U.S. patent application Ser. No. (Attorney's Docket No. D-2781) filed on even date herewith, discloses additional features which can be used in combination with the present apparatus and methods. The disclosure of this application, in its entirety, is incorporated by reference herein.

Each individual feature and each combination of two or more features described herein are included within the scope of the present invention provided that the features included in the combination are not mutually inconsistent.

These and other aspects and advantages of the present invention are set forth in the following detailed description and claims, particularly when considered in conjunction with the accompanying drawings in which like parts bear like reference numerals.

DETAILED DESCRIPTION OF THE DRAWINGS

Figure 1:
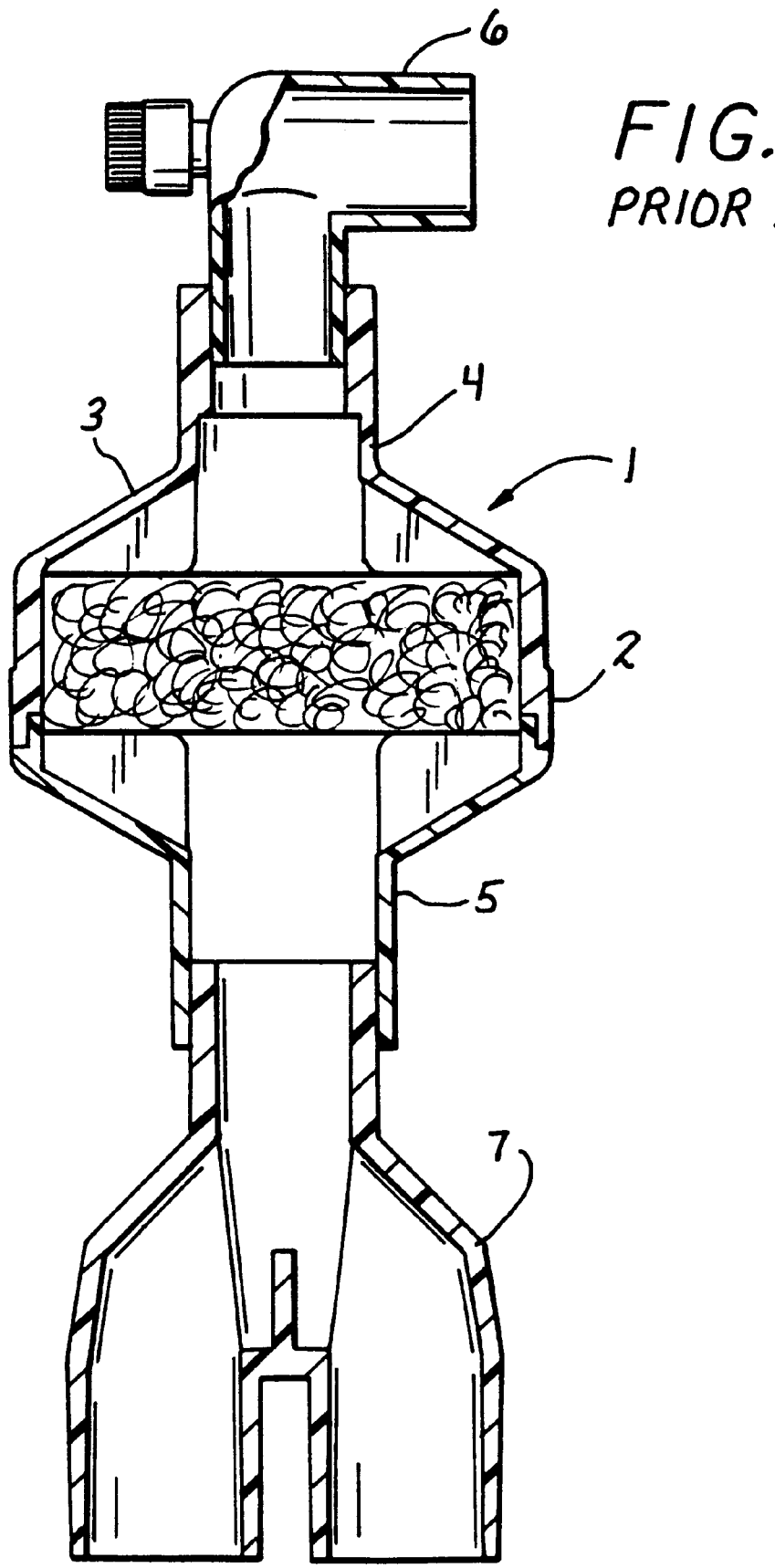
FIG. 1 is a front side view, partly in cross section of a prior art device used to exchange heat and moisture with respiratory gases.

With reference to FIG. 1, an example of a commercially available HME unit, shown generally at 1, includes a heat and moisture exchange (HME) member 2 enclosed in a housing 3 including an inlet 4 and an outlet 5. An elbow fitting 6 is connected to the inlet 4 of the housing 3. This elbow fitting 6 is adapted to be connected to a tracheal tube device, not shown.

A manifold 7, adapted to be connected to a device for passing respiratory gases, is connected to the outlet 5 of housing 3.

One important disadvantage of the prior art device 1 is the substantial amounts of open or dead space located both above and below the HME member 2. Such space is detrimental for a number of reasons. For example, this dead space allows for heat transfer to the environment surrounding the HME unit 1, which reduces the heat transfer effectiveness of the respiratory gases passing into the patient in whom the tracheal tube device is located. Moisture condensation can also result, thereby reducing the amount of humidification in the respiratory gases being passed to the patient. Further, the size or bulkiness of the HME unit 1 may make it difficult to handle during use and may also be a physical impediment or obstacle during the surgery or other treatment of the patient.

Figure 2:
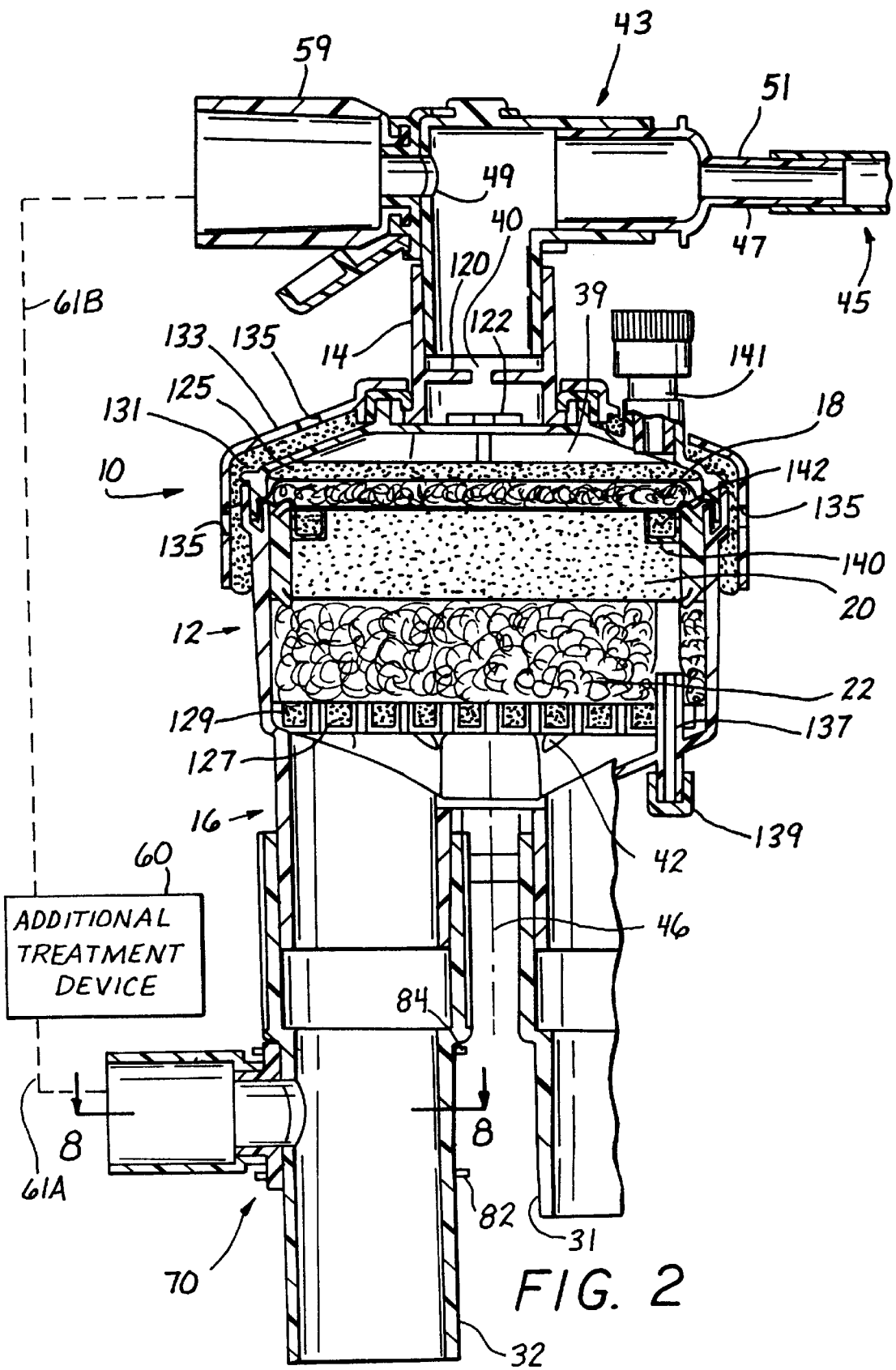
FIG. 2 is a front view, partly in cross section, of an embodiment of an apparatus in accordance with the present invention.

An embodiment of the apparatus in accordance with the present invention is shown in FIG. 2. This apparatus, shown generally at 10, includes a housing 12 having an inlet 14 and a two tube outlet 16. Apparatus 10 also includes a filter element 18, generating material 20 and a gas permeable member 22.

The tracheal tube device 45 is connected to the inlet 14 of the apparatus 10 via fitting 43. The outlet 16 of the apparatus 10 is joined or connected to two tubes 31 and 32 with communicate with an anesthesia machine or a ventilator (not shown). In this arrangement, the patient is provided with respiratory gases from the anesthesia machine or ventilator through inspiratory tube 32. Such gases pass into the apparatus 10, and through tracheal tube device 45 into the trachea of patient. Exhaled respiratory gases passed from the trachea through the tracheal tube device 45 and the apparatus 10 and into the expiratory tube 31. This cycle is repeated each time the patient inhales and exhales respiratory gases.

Housing 12 can be made of any suitable material of construction. Preferably, housing 12 is made of polymeric material. The housing 12 is configured or structured so as to minimize the amount of open or dead space above filter element 18 and below gas permeable member 22. This provides for more efficient and effective heat and moisture transfer, for example, relative to commercially available HME unit 1. In addition, the size of apparatus 10 is small relative to the size of HME unit 1. This provides for relative ease in using the apparatus 10 and reduces the amount of space taken up by the apparatus.

Fitting 43 is connected to both inlet 14 and tracheal tube device 45. Tracheal tube device 45 is joined directly to first end 47 of fitting 43. Located directly opposite first end 47 is a second end opening 49 which is substantially aligned with the opening 51 defined by first end 47.

Figure 4:
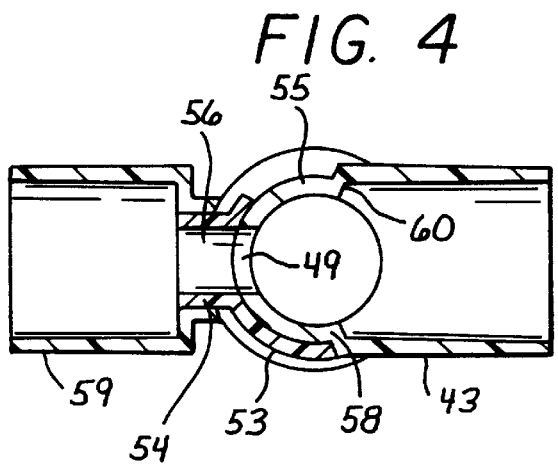
FIG. 4 is a partial top view of the fitting and complimentary adaptor (closure assembly) shown in FIG. 3.
Figure 5:
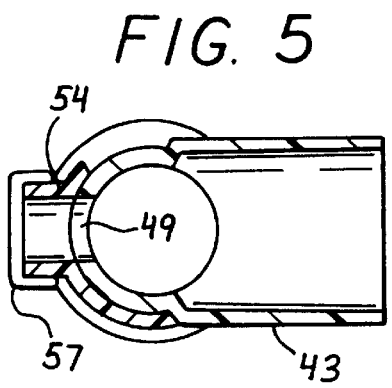
FIG. 5 is a partial top view of the fitting shown in FIG. 2 with a cap covering the port.

With particular reference to FIG. 4, a rotatable closure element 53 is positioned and carried on the second end 55 of fitting 43. Closure element 53 includes a closure outlet or through port 54. By rotating closure element 53 about second end 55, second end opening 49 can be either opened or closed to the passageway 56 defined by closure outlet 54. In addition, even if second end opening 49 is opened, a cap 57, which is secured to fitting 43, can be placed on closure outlet 54 to cover the through port. This feature is shown in FIG. 5. Rotatable closure element 53 rotates between first stop 58 and second stop 60 on fitting 143. When the closure element 53 is in contact with first stop 58, second end opening 49 is in fluid communication with closure outlet 54. When the closure element 53 is in contact with second stop 60, second opening 49 is out of fluid communication with closure outlet 54.

As shown in FIGS. 2 and 4, second end opening 49 can be opened and in fluid communication with a tube 59 which is effective in providing an additional treatment to the patient, as is discussed hereinafter. One of the advantages of the rotatable closure element 53 is that an additional treatment device 60, for example, a nebulizer, can be connected to the closure element 53 while the second opening 49 is closed. Thus, the additional treatment device 60 can be pressurized so that when the rotatable closure element 53 is moved to open the second end opening 49, little or no disruption to the patient's breathing occurs. This is an important advantage over the prior art in which the system is depressurized prior to providing a secondary treatment to the patient.

Figure 6:
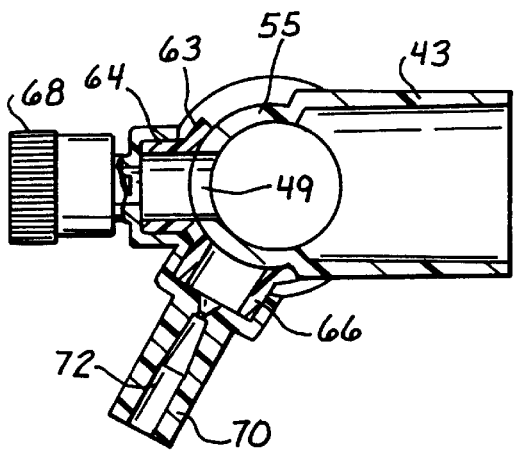
FIG. 6 is a top view of an alternate fitting including two access ports.
Figure 7:
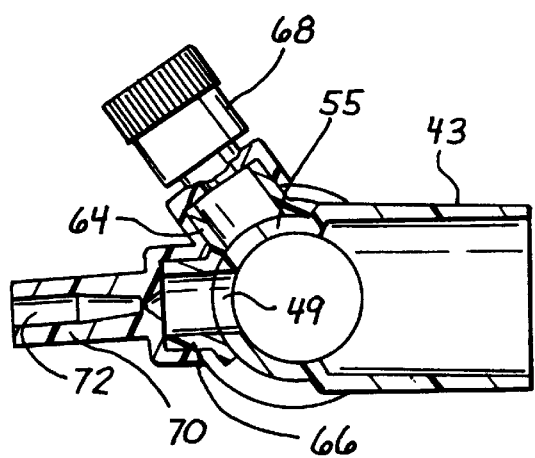
FIG. 7 is a partial top view of the fitting shown in FIG. 6 in an alternate position.

FIGS. 6 and 7 illustrate a modified rotatable closure element 63 which includes a first closure outlet 64 and a spaced apart second closure outlet 66. Thus, by rotating modified closure element 63 about second end 55 of fitting 43, second end opening 49 can be opened to either first closure outlet 64 or second closure outlet 66. Even if second end opening 49 is opened to first closure outlet 64, the system can be closed by placing cap 68 over the first closure outlet, as shown in FIG. 6. Second closure outlet 66 is fitted with an adaptor 70 defining an elongated hollow space 72. The combination of second closure outlet 66 and adaptor 70 is particularly effective in sampling respiratory gases flowing in fitting 43. Of course, if desired, a cap can be placed on the adaptor 70 to insure that no leakage occurs.

In addition, as shown in the shadow lines in FIG. 2, a bypass line 61, for example, made of conventional polymeric tubing, can be provided to provide fluid communication between inspiratory tube 32, the additional treatment device 60 and fitting 43. Thus, if during the additional treatment it is important to avoid one or more materials located in the housing 12, the bypass line 61 and additional treatment device 60 can be used very effectively. Also, one or more medications which would be harmed if passed through housing 12 can be introduced into this bypass line 61 and passed to the patient without passing through housing 12.

Any suitable valve may be employed to divert inspiratory gases from inspiratory tube 32 into bypass line 61. The valving arrangement shown generally at 70 in FIGS. 2, 8 and 8A involves a so-called sleeve valve. Thus, inspiratory tube 32 includes an outlet opening 74 therethrough. The first portion 61A of bypass line 61 includes a bypass through port 76 and a sleeve 78 which extends outwardly away from the through port 76 and is adapted to come in contact with the outer surface 80 of inspiratory tube 32. Two bands 82 and 84 surround the inspiratory tube 32 and the sleeve 78. Bands 82 and 84 are sufficiently flexible to allow the sleeve 78 to be rotated relative to the exterior surface 80 of inspiratory tube 32.

Figure 8:
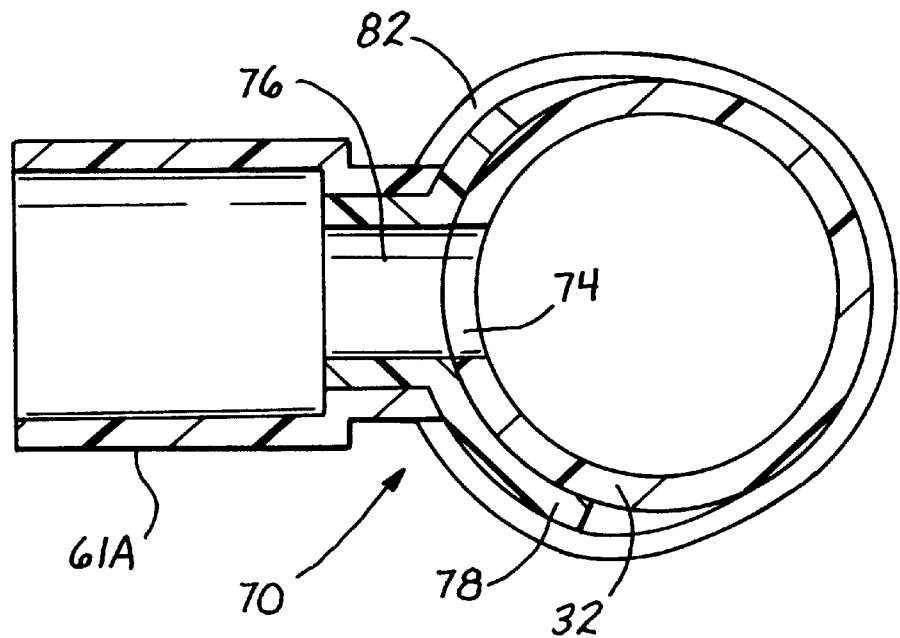
FIG. 8 is a cross-sectional view taken generally along line 8—8 at FIG. 2.
Figure 8A:
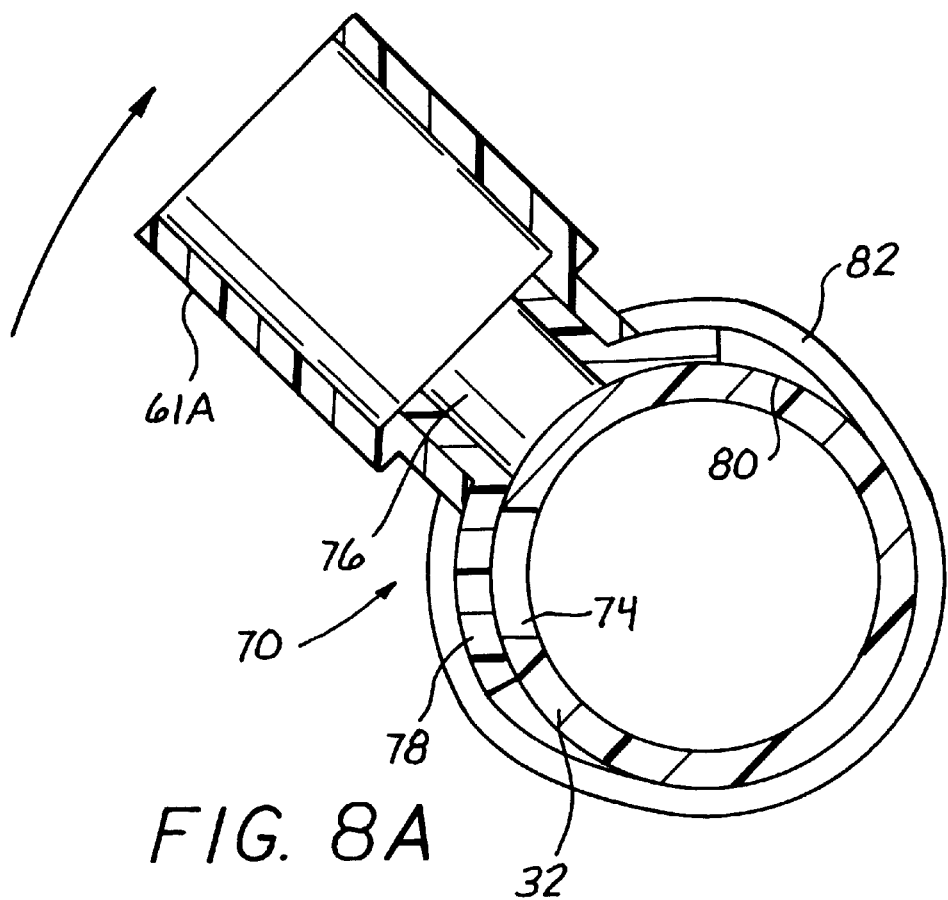
FIG. 8A is a cross-sectional view similar to FIG. 8 with the valve in an alternate position.

Thus, in normal operation of apparatus 10, that is with the additional treatment device 59 being inoperative, the sleeve 78 and inspiratory tube 32 are mutually oriented as shown in FIG. 8A. In this configuration, the through port 76 is not in fluid communication with the outlet opening 74. Thus, all of the inspiratory gases pass through housing 12.

When it is desired to provide the patient with an additional treatment, for example, a nebulizer treatment, the sleeve 78 is rotated relative to the exterior surface 80 of inspiratory tube 32, to a position as shown in FIG. 8. In this position, a substantial portion, and even substantially all, of the inspiratory gases passing through inspiratory tube 32 pass through outlet opening 74 through the through port 76 into first portion 61A of bypass line 61. At substantially the same time, closure element 53 is rotated to provide fluid communication between second portion 59 of bypass line 61 and the additional treatment device 60. In this manner, the patient receives an additional treatment without the complication of having the additional treatment pass through the housing 12. After the additional treatment, the sleeve 78 is rotated again to the position shown in FIG. 8A, closure element 53 is rotated to close second end opening 49, and apparatus 10 is used in its normal configuration.

A hollow chamber 39 is formed by the housing 12. Located within the chamber 39 and extending substantially across the entire cross-section of the chamber are the antimicrobial filter element 18 which is secured to the housing 12, a quantity of particulate generating material 20, in particular, particulate carbon dioxide absorbing material, and a gas permeable member 22, in particular a fibrous member.

Respiratory gases from the patient pass through inlet passage 40 defined by inlet 14 and into chamber 39. Inlet 14 is part of housing 12. Such respiratory gases pass through filter element 18, generating material 20 and gas permeable member 22 before exiting through outlet passage 42 defined by outlet 16. Outlet 16 is part of housing 12. When respiratory gases are to be inhaled by the patient 30, such gases pass into apparatus 10 through outlet passage 42 into chamber 39, across gas permeable member 22, generating material 20 and filter element 18. This respiratory gas to be inhaled is passed through inlet passage 40 into tracheal tube device 45 and into the trachea of the patient.

The filter element 18, generating material 22 and gas permeable member 22 are all positioned substantially perpendicular to the longitudinal axis 46 of apparatus 10. Thus, the filter element 18, generating material 20 and gas permeable member 22 are all substantially perpendicular to the general direction of flow between the inlet passage 40 and the outlet passage 42.

The filter element 18 may be of any suitable configuration to remove contaminants from the respiratory gas passing therethrough. The filter element 18 should be sufficiently gas permeable so that the respiratory gases passing therethrough result in a relatively reduced, or even minimal pressure differential. The filter element 18 may be chosen from filter material used in conventional respiratory filters or heat and moisture exchangers for respiratory gases, many of which are known and commercially available. The filter element 18 may have antimicrobial activity.

The gas permeable member 22 is selected to provide for both heat and moisture exchange with gases passing through the housing 12. The gas permeable member may be chosen from any suitable material which is effective as a heat and moisture exchanging material and has gas permeability. Examples of useful materials from which gas permeable member 22 can be chosen include such materials which are conventionally used in heat and moisture exchangers for respiratory gases, many of which are well known and commercially available.

The generating material 20, which is located between and adjacent the filter element 18 and the gas permeable member 22, is effective to generate both water and heat, preferably in response to an interaction with carbon dioxide, for example, absorption of and subsequent reaction with carbon dioxide, in the respiratory gas which comes in contact with the generating material. The carbon dioxide generating material making up generating material 22 preferably is in the form of particles which are effective to absorb, or otherwise interact with, carbon dioxide in the respiratory gases. The generating material 20 preferably is sufficiently gas permeable so that respiratory gases passing therethrough result in a substantially reduced, or even in a minimal pressure differential.

Without wishing to limit the invention to any particular theory of operation, it is believed that the generating material is effective to neutralize carbon dioxide with resultant production of heat and water. Using one particularly useful carbon dioxide absorbing generating material, such neutralization is believed to proceed as follows:

$$CO_2 + H_2O \rightleftharpoons H_2CO_3 \tag{I}$$

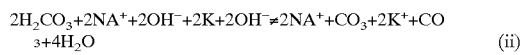

$$2H_2CO_3 + 2NA^+ + 2OH^- + 2K + 2OH^- \rightleftharpoons 2NA^+ + CO_3 + 2K^+ + CO_3 + 4H_2O \tag{ii}$$

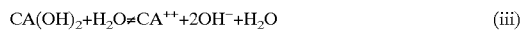

$$CA(OH)_2 + H_2O \rightleftharpoons CA^{++} + 2OH^- + H_2O \tag{iii}$$

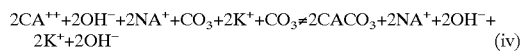

$$2CA^{++} + 2OH^- + 2NA^+ + CO_3 + 2K^+ + CO_3 \rightleftharpoons 2CACO_3 + 2NA^+ + 2OH^- + 2K^+ + 2OH^- \tag{iv}$$

In (I) the $CO_2$ dissolves at a rate governed by a number of physical chemical factors. The rate is not proportional to the partial pressure of the $CO_2$ which is in contact with the film of moisture coating the soda lime granules, but greater—because some of the $CO_2$ combines chemically with the water to form carbonic acid. The rate is directly proportional to the rate of removal of dissolved $CO_2$, or carbonic acid, from solution, by reaction with hydroxyl ion (reaction ii). Thus, the rapidity of removal of dissolved $CO_2$ is directly related to the availability of hydroxy ions. Since the reaction between H+ and OH– is instantaneous, forming water, reaction (iii) and (iv) must supply additional hydroxyl ions to keep the absorption of $CO_2$ progressing. The latter two reactions are therefore rate limiting.

In a very useful embodiment, the amount of generating material present is effective to generate only a portion, more preferably a minor portion (that is, no more than about 50%), of the water to humidify respiratory gases passing through the housing. In particular, the amount of generating material present in the housing is effective to generate at least about 5%, more preferably at least about 10%, and still more preferably at least about 15% of the water to humidify respiratory gases passing through the housing. On the other hand, the amount of generating material present in the housing preferably is effective to generate no more than about 50% of the moisture of the water to humidify respiratory gases passing through the housing. Having excessively large amounts generating material present in the housing can result in the respiratory gases passing to the patient having a temperature which is excessively high relative to the requirements of the patient. Therefore, it is preferred that only relatively reduced amounts of water and heat, as described herein, be generated by the generating material. In the event carbon dioxide absorbing material is used as the generating material, the present apparatus preferably initially includes about 10 or about 20 grams to about 40 or about 60 or about 80 grams, more preferably about 20 grams to about 30 or about 40 grams of such material, particularly when the patient in question is an adult human being. The amount of generating material used when the patient is a human infant or a premature human infant may be somewhat less because of the very small lung tidal volumes, for example, about 10 cc or less, involved.

This controlled or limited amount of water and heat generation makes it important to provide not only the generating material but also the gas permeable member, e.g., a conventional HME member, which acts in combination with the generating material to provide the desired, preferably controlled and acceptable, degree of humidification and heating to the respiratory gases being passed to the patient.

Because the generating material preferably interacts with carbon dioxide in the respiratory gases to generate the water, and preferably heat, the amount of carbon dioxide being exhaled by the patient provides a suitable control as to the amount of water, and preferably heat, generated by the generating material. Thus, increased respiration by the patient, which results in increased production of carbon dioxide, leads to increased water, and preferably heat, generation, which is useful in humidifying and heating the increased amounts of respiratory gases required by the patient. With the generating material generating water, and preferably heat, because of an interaction with carbon dioxide, the patient and his/her respiratory needs, in effect, control the amount of water, and preferably heat, being generated in the present apparatus.

The generating material preferably is positioned in the housing adjacent the gas permeable member. In a very useful embodiment, the generating material is located nearer to the inlet than is the gas permeable member. Thus, exhaled gases from the patient preferably come in contact with the generating material before being passed to the gas permeable member. This arrangement is effective to provide that at least a portion of the water and heat generated by the generating material is accumulated or collected by the gas permeable member and is available for use in humidifying and heating the respiratory gases being passed to the patient.

The generating material in the housing is often of such a character that after a period of time in service (in the present apparatus) a deactivated material is formed. For example, the generating material may include one or more active components which are consumed and/or otherwise rendered ineffective to generate water, and preferably heat, after time in service in the present apparatus. The deactivated material is derived from the generating material and preferably includes such consumed and/or otherwise ineffective components. In any event, the deactivated material has substantially no ability to generate water or heat available to humidify or heat respiratory gases passing through the housing. However, it has been found that the present apparatus including the deactivated material in place of the generating material has a greater ability to humidify and heat respiratory gases passing through the housing relative to an identical apparatus without either the generating material or the deactivated material.

Without wishing to limit the invention to any particular theory of operation, it is believed that the deactivated material, even though it is ineffective to generate water and heat, is at least to some extent effective to transfer, e.g., store or collect and release, moisture and heat with the respiratory gases passing through the housing. The apparatus with the deactivated material in place of the generating material has increased moisture/heat transfer capacity relative to an identical apparatus without either the generating material or the deactivated material. The present apparatus provide substantial benefits even though the generating material is rendered ineffective and forms the deactivated material.

Although any suitable component or combinations of components may be useful in generating material 20 to generate moisture and heat, it is preferred that the generating material be that sold by W. R. Grace under the trademark "SODA SORB".

Apparatus 10 includes a set of kinetic energy reducing baffles 120 and 122, located in inlet 14, which are effective to reduce the kinetic energy of mucous from the patient. The mucous tends to pool around the periphery of the chamber 39 and can be effectively suctioned out via port 141. This increases the effective useful life of apparatus 10. In addition, inlet 14 is rotatable about housing 12. This reduces the stress on the tracheal tube device 45 when housing 10 is moved or otherwise disturbed.

In addition, housing 12 includes a layer of hydrophilic open cell foam material 125 which is located between filter element 18 and inlet 14. Further, a tray-like element 127 including a quantity of hygroscopic material 129, for example, calcium chloride and the like, is located in housing 12 between gas permeable member 22 and outlet 16. The exterior of housing 12 includes a layer of heat generating material 131. The particles of heat generating material 131 can be, for example, particles of iron and/or other metal or metals, active carbon and the like, which are effective, when exposed to oxygen, to generate heat. Layer 131 substantially surrounds the upper or inlet portion of housing 12, and extends downwardly to approximately the level between the generating material 20 and gas permeable member 22. A heat reflective cover shell 133, for example, made of a polymer material having a heat reflective substance coated on the inner surface of the shell, is located on housing 12 so as to cover the heat generating material layer 131. Cover shell 133 includes through holes 135 located around the cover shell so as to provide access for oxygen to the heat generating material, thereby allowing heat to be generated from this material.

Housing 12 includes a hollow tubular construction 137 which extends from outside the chamber 39 defined by the housing to inside the chamber. A cap 139 covers the tubular construction 137. The cap 139 can be removed to allow water to be passed through tubular construction 137 to the chamber 39. The tubular construction 137 can be considered a reservoir for water to be used in housing 12, as well as a conduit to provide this water to the chamber 39. In addition, port 141 can be employed to add water directly to the hydrophilic foam layer 125. An annular ring 140 is situated near the top of generating material 620, and holds a buffering material 142, for example, a conventional pH buffer, which acts to modulate the pH (acidity/alkalinity) of liquid water condensed or otherwise present in the housing 612 toward a neutral pH of 7. The ring 140/buffering material 142 combination may be situated at other locations in the housing 612, for example, between the filter 618 and hydrophilic foam layer 125.

Because of the presence of the heat generating material 131, the apparatus 10 is shipped and stored in packaging which is not permeable to oxygen. Also, the apparatus 10 is, during shipment and storage, maintained substantially totally dry. Thus, when it is desired to use apparatus 10, it is removed from the packaging and secured to the tracheal tube device and the tubes for providing respiratory gases. In order to reduce the "start up" phase of the operation of apparatus 10, water is added to the hydrophilic foam material layer 125 through port 141. Such added water is quite effective during "start up" of an apparatus which does not include generating material 20. Removing the apparatus 10 from the packaging causes oxygen to contact the heating material in layer 131 which generates heat that is transferred inwardly into the chamber 39. Thereafter, the heat generating material layer 131 continues to provide heat to chamber 39, thereby assisting in heating the respiratory gases being passed to the patient. In addition, detrimental heat loss from chamber 39 through housing 12 is reduced.

Figure 3:
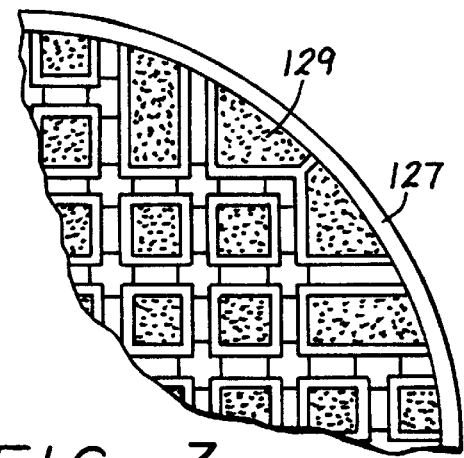
FIG. 3 is a partial top view of a tray-like member included in the apparatus shown in FIG. 2.

The hygroscopic material 129 is very effective in assisting the apparatus 10 during initial or "start-up" operation of the apparatus. The hygroscopic material 129 comes in contact with water from respiratory gases passing through the housing 12 and produces heat which is available for transfer to the respiratory gases being passed to the patient. The location of the hygroscopic material 129 near the outlet 16 of housing 12 is beneficial in that moisture which interacts with the hygroscopic material to generate heat would, if not so interacted, be removed from the apparatus 10 and become unavailable to the patient. Placing the hygroscopic material 129 at this location, therefore, provides a substantial benefit to the patient from moisture which would otherwise be lost to the patient. The tray-like element 127, shown in detail in FIG. 3, is constructed so that respiratory gases passing out of the housing 12 contact the hygroscopic material 129 and interact to generate heat. As respiratory gases move into the housing 12 across tray-like element 127, such gases pick up the heat produced by the hygroscopic material 129 and provide warmed respiratory gases to the patient.

The present apparatus are directed to providing respiratory gases to a patient undergoing surgery or other treatment procedure. The apparatus effectively provide heat and moisture to such respiratory gases so as to reduce the risk of trauma to the patient and increase the patient's comfort and safety. Moreover, the present apparatus are very flexible in use, preferably being adapted to provide an additional treatment or additional treatments to a patient with reduced disruption in the patient's respiration support, reduced patient trauma and reduced clinician anxiety.

While this invention has been described with respect to various specific examples and embodiments, it is to be understood that the invention is not limited thereto and that it can be variously practiced within the scope of the following claims.

What is claimed is:

1. An apparatus for heating and humidifying respiratory gases passed to a patient comprising:
   a housing having a first port adapted for passing respiratory gases between the housing and a patient and a second port adapted for connection to a tube for passing respiratory gases to and from the patient, the first port and the second port being positioned so that respiratory gases passing to and from the patient through the housing pass therebetween;
   a gas permeable member positioned in the housing between the first port and the second port and adapted to exchange heat and moisture with respiratory gases passing through the housing;
   a fitting joined to both the housing and a tracheal tube device, the fitting including a separate opening through which an additional treatment is provided to the patient; and
   a fitting closure assembly coupled to the fitting and including a through port adapted to be coupled to a device for providing the additional treatment, the fitting closure assembly being movable between a first position in which the separate opening is not in fluid communication with the through port, and a second position in which the separate opening is in fluid communication with the through port.

2. The apparatus of claim 1 wherein the fitting closure assembly is rotatable relative to the fitting, the rotation of the fitting closure assembly moving the fitting closure assembly between the first and second positions.

3. The apparatus of claim 1 which further comprises a cap assembly adapted to cover the through port when the through port is not coupled to a device for providing an additional treatment.

4. The apparatus of claim 3 wherein the cap assembly is secured to the fitting.

5. The apparatus of claim 1 wherein said fitting closure assembly includes a spaced apart second through port through which respiratory gases are monitored.

6. The apparatus of claim 5 wherein the fitting closure assembly in the first position provides fluid communication between the separate opening and the second through port.

7. The apparatus of claim 2 wherein the fitting closure assembly is rotatable relative to the fitting between spaced apart first and second rotation stops located on the fitting.

8. The apparatus of claim 1 which further comprises a filter element located in the housing and adapted to filter respiratory gases passing through the housing.

9. The apparatus of claim 1 which further comprises a generating material located in the housing between the first port and the second port and adapted to generate water available to humidify respiratory gases passing through the housing, and the first port is further adapted for connection to a tracheal tube device.

10. The apparatus of claim 9 which further comprises a hygroscopic component positioned in the housing separate and apart from the gas permeable member and the generating material and being adapted to generate heat available to heat respiratory gases passing through the housing.

11. An apparatus for heating and humidifying respiratory gases passed to a patient comprising:

a housing having a first port adapted for passing respiratory gases between the housing and a patient and a second port adapted for connection to a tube for passing respiratory gases to and from the patient, the first port and the second port being positioned so that respiratory gases passing through the housing pass therebetween;

a filter element located in the housing and adapted to filter respiratory gases passing through the housing;

a gas permeable member positioned in the housing between the first port and the second port and adapted to exchange heat and moisture with respiratory gases passing through the housing;

a fitting joined to both the housing and a tracheal tube device, the fitting including a separate opening through which an additional treatment is provided to the patient;

a bypass line including a first portion adapted to be connected to and in fluid communication with both a tube for passing inspiratory gases and a device for providing the additional treatment and a second portion adapted to be connected to and in fluid communication with a device for providing the additional treatment and the fitting; and a valve adapted to be moved between a closed position in which no gas flow occurs through the bypass line and an open position in which inspiratory gases from a tube for passing inspiratory gases to the fitting flows through the bypass line.

12. The apparatus of claim 10 wherein the valve is positioned to move between the closed position in which the first portion of the bypass line is not in fluid communication with a tube for passing inspiratory gases and the open position in which the first portion of the bypass line is in fluid communication with a tube for passing inspiratory gases.

13. The apparatus of claim 12 wherein the valve comprises a sleeve valve secured to a tube for passing inspiratory gases.

14. The apparatus of claim 11 which further comprises a fitting closure assembly coupled to the fitting and including a through port adapted to be coupled to and in fluid communication with the second portion of the bypass line, the fitting closure assembly being movable between a first position in which the separate opening is not in fluid communication with the through port and a second position in which the separate opening is in fluid communication with the through port.

15. The apparatus of claim 14 wherein the fitting closure assembly is rotatable relative to the fitting, the rotation of the fitting closure assembly moving the fitting closure assembly between the first and second positions.

16. The apparatus of claim 15 wherein the fitting closure assembly is rotatable relative to the fitting between spaced apart first and second rotation stops located on the fitting.

17. The apparatus of claim 11 which further comprises a generating material located in the housing between the first port and the second port and adapted to generate water available to humidify respiratory gases passing through the housing, and the first port is further adapted for connection to a tracheal tube device.

18. A method for heating and humidifying respiratory gases passed to a patient and for providing an additional treatment to the patient which comprises:

operating the apparatus of claim 11 so that the fitting is joined to a tracheal tube located within the patient, thereby providing respiratory gases to the patient;

providing a device for providing the additional treatment to the patient;

causing inspiratory gases from a tube for passing inspiratory gases to pass through the bypass line into the fitting; and operating the device for providing the additional treatment to the patient so as to provide the additional treatment to the patient through the second portion of the bypass line.

19. The method of claim 18 which further comprises preventing inspiratory gases passing through the bypass line, and causing the device for providing the additional treatment to the patient to be inoperative.

20. The method of claim 18 wherein the apparatus further comprises a fitting closure assembly coupled to the fitting and including a through port adapted to be coupled to and in fluid communication with the second portion of the bypass line, the fitting closure assembly being movable between a first position in which the separate opening is not in fluid communication with the through port and a second position in which the separate opening is in fluid communication with the through port, and the fitting closure assembly is moved from the first position to the second position after the causing step is initiated.

* * * * *